(12) United States Patent
Whited et al.

(10) Patent No.: US 9,488,552 B2
(45) Date of Patent: Nov. 8, 2016

(54) CUTTING APPARATUS FOR AUTOMATED TISSUE SAMPLE PROCESSING AND IMAGING

(71) Applicant: CERNER INNOVATION, INC., Kansas City, KS (US)

(72) Inventors: Robert E. Whited, Kansas City, MO (US); John David L. Nolen, Prairie Village, KS (US); Sameer Bhatia, Omaha, NE (US)

(73) Assignee: Cerner Innovation, Inc., Kansas City, KS (US)

( * ) Notice: Subject to any disclaimer, the term of this patent is extended or adjusted under 35 U.S.C. 154(b) by 174 days.

(21) Appl. No.: 14/496,052

(22) Filed: Sep. 25, 2014

(65) Prior Publication Data

US 2016/0091400 A1 Mar. 31, 2016

(51) Int. Cl.
*A61B 10/00* (2006.01)
*G01N 1/28* (2006.01)

(52) U.S. Cl.
CPC ....... *G01N 1/286* (2013.01); *G01N 2001/2873* (2013.01)

(58) Field of Classification Search
CPC ....................................................... G01N 1/286
See application file for complete search history.

(56) References Cited

U.S. PATENT DOCUMENTS

| | | | |
|---|---|---|---|
| 2,461,621 A | 2/1949 | Allen | |
| 3,902,390 A | 9/1975 | Darbo | |
| 5,226,334 A | 7/1993 | Pegoraro | |
| 7,372,985 B2 | 5/2008 | So et al. | |
| 7,677,289 B2 | 3/2010 | Hayworth et al. | |
| 7,724,937 B2 | 5/2010 | So et al. | |
| 7,866,464 B2 | 1/2011 | Miyatani et al. | |
| 8,165,363 B2 | 4/2012 | Soenksen et al. | |
| 8,351,675 B2 | 1/2013 | So et al. | |
| 8,463,741 B2 | 6/2013 | Ehlke et al. | |
| 8,499,673 B2 | 8/2013 | Keller | |
| 8,571,286 B2 | 10/2013 | Soenksen et al. | |
| 8,718,351 B2 | 5/2014 | So et al. | |
| 8,839,700 B2 | 9/2014 | Chen et al. | |
| 2009/0252398 A1 | 10/2009 | Luther et al. | |
| 2011/0199187 A1 | 8/2011 | Davidowitz | |
| 2012/0072452 A1 | 3/2012 | Stratman et al. | |

(Continued)

OTHER PUBLICATIONS

Kurabo, Auto Slide Preparation System, last accessed Nov. 10, 2014, 1 page. http://www.kurabo.co.jp/bio/English/product/products.php?M=D&PID=58.

(Continued)

*Primary Examiner* — Jyoti Nagpaul
(74) *Attorney, Agent, or Firm* — Shook, Hardy & Bacon L.L.P.

(57) ABSTRACT

An apparatus is provided for cutting a tissue sample into a plurality of sections for automated tissue sample processing. The apparatus comprises a cutting mechanism and a holding mechanism. The cutting mechanism comprises a blade having a first reference line that extends from an attachment point of the blade to a rotation mechanism to an outermost point of the blade, and the rotation mechanism having a second reference line that extends from an axis point of the rotation mechanism to the attachment point, wherein the blade rotates around the axis point. The holding mechanism causes the tissue sample to remain stationary while the blade makes, at least, a first rotation around the axis point, resulting in a first tissue section cut from the tissue sample.

12 Claims, 11 Drawing Sheets

(56) References Cited

U.S. PATENT DOCUMENTS

2014/0023993 A1 1/2014 Zeng et al.
2014/0026683 A1 1/2014 Hayworth et al.

OTHER PUBLICATIONS

Wang et al., Tissue Refractive Index as Marker of Disease, Journal of Biomedical Optics 16(11), 116017 (Nov. 2011), last accessed Nov. 10, 2014, 8 pages. http://light.ece.illinois.edu/wp-content/uploads/2011/11/Tissure-Refractive-index-as-marker-of-disease.pdf.

Histoindex Core Technology, last accessed Nov. 10, 2014, 1 page. http://histoindex.com/page1.aspx?no=1107.

First Action Interview Preinterview Communication dated Feb. 24, 2016 in U.S. Appl. No. 14/496,063, 4 pages.

Notice of Allowance dated Dec. 31, 2015 in U.S. Appl. No. 14/496,069, 14 pages.

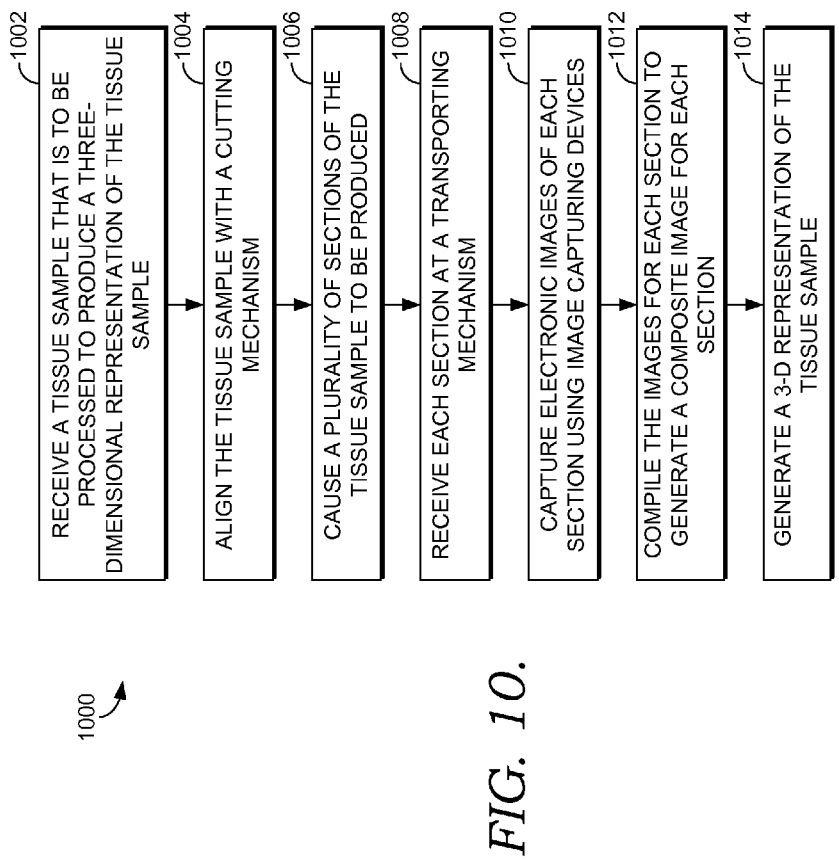

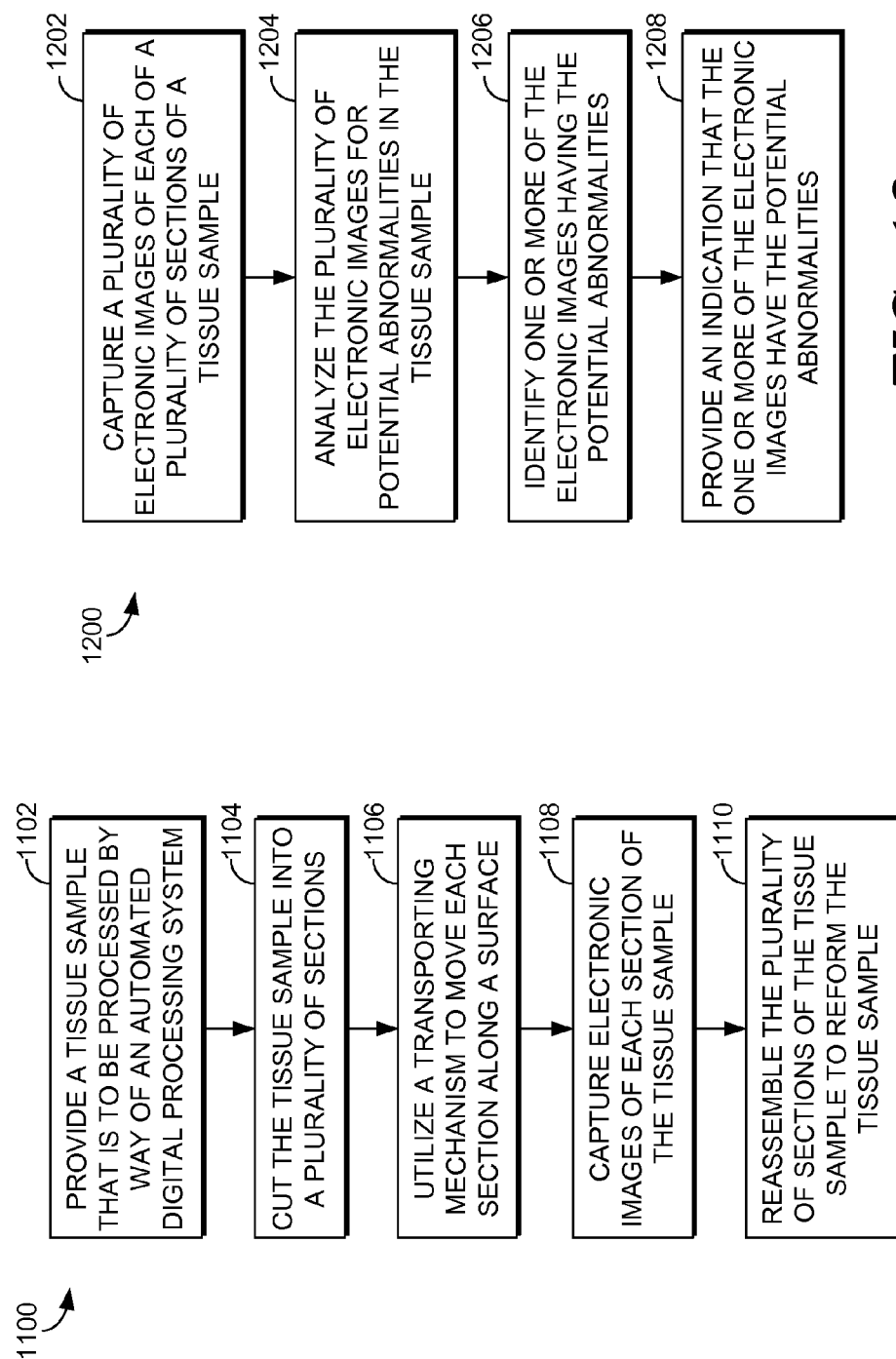

CUTTING APPARATUS FOR AUTOMATED TISSUE SAMPLE PROCESSING AND IMAGING

CROSS-REFERENCE TO RELATED APPLICATIONS

This application is related by subject matter to U.S. patent application Ser. No. 14/496,063 filed even date herewith and entitled "SYSTEMS FOR AUTOMATED TISSUE SAMPLE PROCESSING AND IMAGING", and to U.S. patent application Ser. No. 14/496,069 filed even date herewith and entitled "METHODS FOR AUTOMATED TISSUE SAMPLE PROCESSING AND IMAGING", which are assigned or under obligation of assignment to the same entity as this application, and are incorporated by reference in their entirety into this application.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for processing tissue samples without the use of glass slides, staining, and the like. In one embodiment, a tissue sample is cut into sections for analysis by a rotating blade, where the tissue sample remains stationary during each cut. Once cut, the tissue sections are placed onto a surface of a transporting mechanism that moves the sections so that images can be captured of the tissue sections at different angles, positions, at different wavelengths, etc. The images captured for each tissue section are compiled to generate a composite image. The composite images are used to generate a three-dimensional representation of the tissue sample so that a medical practitioner is able to utilize the three-dimensional representation to identify potential abnormalities, just as would occur with the analysis of the physical tissue sections. However, in this case, it is unnecessary to stain the tissue sections, as the image capturing devices are configured to capture electromagnetic energy within various spectral bands, which allows for abnormalities to be detected when cells react with electromagnetic energy at different wavelengths.

BRIEF DESCRIPTION OF THE DRAWINGS

Embodiments are described in detail below with reference to the attached drawings figures, wherein:

FIG. 10 is a flow diagram of a method for performing automated digital processing of a tissue sample, in accordance with an embodiment of the present invention;

FIG. 11 is a flow diagram of another method for performing automated digital processing of a tissue sample, in accordance with an embodiment of the present invention; and FIG. 12 is a flow diagram of another method for performing automated digital processing of a tissue sample, in accordance with an embodiment of the present invention.

DETAILED DESCRIPTION

Figure 1:
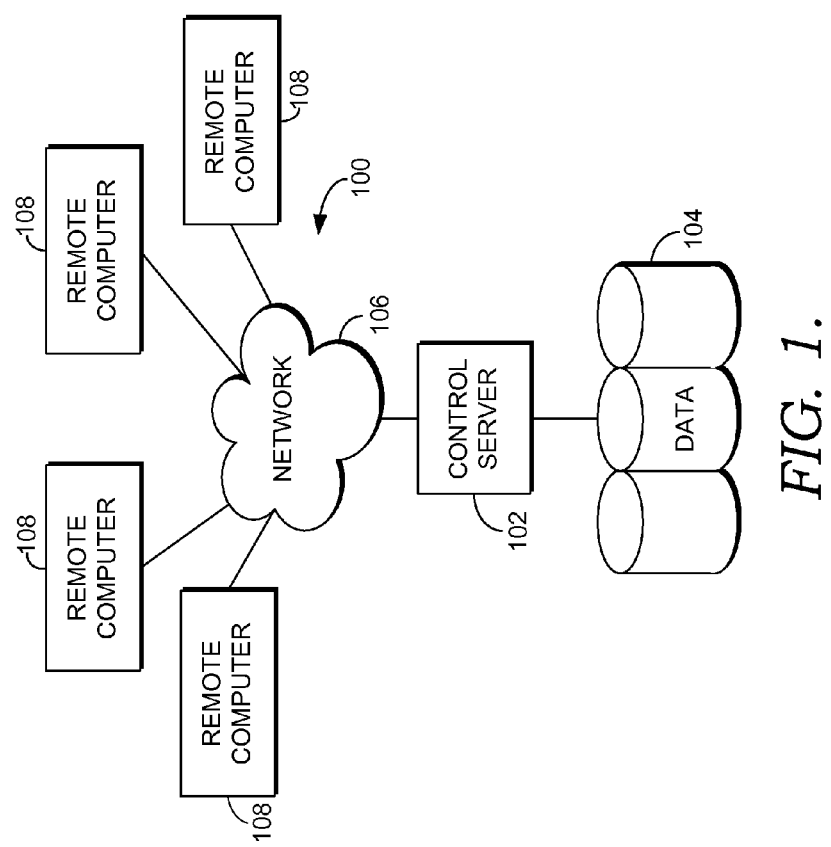
FIG. 1 is a block diagram of an exemplary computing system suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for performing automated processing of tissue samples. In embodiments, the automated processing of a tissue sample comprises cutting sections from the tissue sample, capturing electronic images of the sections, and generating a three-dimensional representation of the electronic images. The three-dimensional representation can be used for diagnostic purposes with or without the physical tissue sections cut from the tissue sample. While typically a tissue sample is cut into sections (e.g., by use of a microtone), the sections are placed on a glass slide, are then stained, and the pathologist examines each slide under a microscope, in embodiments described herein, the tissue sections are not stained. Instead, high-speed imaging devices are utilized that are able to capture photons reflected off of the tissue sections that are within various frequency ranges. In embodiments, one or more emitting sources are used to emit electromagnetic radiation. The image capturing devices are then able to capture the electromagnetic energy reflected off of the tissue section surfaces. The electromagnetic energy reflected off of the tissue section surfaces results in the capture of detail (e.g., color, luminosity, contrast) by way of the image capturing devices, including visible light, ultraviolet, x-ray, infrared, microwave, radio, and the like. The detail captured by the image capturing devices provides decision support to a medical practitioner's diagnosis of a patient based on the three-dimensional representation generated.

In one embodiment, the tissue sample is cut by way of a cutting mechanism that comprises a blade. Instead of the tissue sample being forced upon a stationary blade to make the cuts, here, the tissue sample remains stationary during the cuts that produce the plurality of tissue sections. In one aspect, the blade rotates and is configured to be positioned such that only a part of the blade makes a first contact with the tissue sample. The angle of the blade with respect to the tissue sample, a rotation mechanism, etc., facilitates a smooth cut of the tissue sample. In one aspect, the tissue sample remains stationary for an entire cutting process, including in between cuts of the tissue sample. As such, here, the blade would be moved in between cuts to facilitate the production of a plurality of tissue sections. But in another aspect, the tissue sample remains stationary during a cut, but is moved in between cuts so that subsequent tissue sections can be produced.

Once a tissue sample has been cut into a plurality of sections, the sections are moved along a surface of a transporting mechanism (e.g., conveyor system). While moving along the surface, the image capturing devices may capture images of the sections at different angles, positions, within different spectral bands, etc. While a single image capturing device may be used, in embodiments, two or more image capturing devices may be used not only to capture the images at different angles or positions, but each image capturing device may be configured to capture electromagnetic energy reflected off of the tissue section surfaces at different frequency bands. Once the images have been captures, the images for each tissue section may be compiled to generate a composite image for each tissue section. These composite images are used to generate the three-dimensional representation of the tissue sample. When a medical practitioner utilizes the three-dimensional representation to support a diagnosis, the medical practitioner may have the ability to cut through the tissue sample at any location and to view the tissue sections at various angles, positions, wavelengths, etc. The result is to provide a simplified and improved experience for the medical practitioner without the need for the physical tissue sections.

After the images have been captured, the tissue sections may be stacked to reproduce the tissue sample, as if the tissue sample had not been cut. This reformed tissue sample can be more efficiently stored, as opposed to storing each tissue section separately, and could even be used to supplement the medical practitioner's use of the three-dimensional representation in identifying potential abnormalities in the cells of the tissue sample. In one embodiment, an abnormality determination engine is utilized to indicate the portions of the tissue sample that contain potential abnormalities. This complements the medical practitioner's own analysis of the three-dimensional representation of the tissue sample.

When we refer to a tissue sample herein, we may refer to a tissue sample alone, or in some embodiments, we refer to a tissue sample that has been embedded in a wax substance, such as paraffin. We may also refer to a tissue sample that has been embedded in wax, and that has been placed on a cassette. The embedding of the tissue sample in wax allows for the tissue sample to be cut in sections whose thicknesses are such that a single layer of cells can be analyzed by way of the electronic images captured of the tissue sections. A tissue sample, as such, may also be referred to as a tissue sample block herein.

As will become apparent, the embodiments described herein provide for an improved way to processing tissue samples. For instance, embodiments enable automated processing of tissue samples where user intervention is not required, while typically tissue sample processing is user and time intensive. Additionally, while tissue sections cut from a tissue sample are typically placed on a glass slide and are stained, embodiments provided herein do not require this, as tissue sections remain unstained throughout the entire process. The automated process described herein requires less time and expense than traditional methods of processing tissue samples.

Additionally, traditional methods of cutting tissue samples and extremely time and user intensive. Further, the tissue sample or sections cut from the tissue sample can be chaffed or even be destroyed, as the tissue sample is typically forced down upon a stationary blade. As described herein, a rotating blade that is angled from the cutting surface of the tissue sample cuts through the stationary tissue sample to provide a smoother cut, lessening the risk of chaffing and destruction of the tissue sections that are to be analyzed.

A first aspect is directed to an apparatus for cutting a tissue sample into a plurality of sections. The apparatus comprises a cutting mechanism that includes a blade having a first reference line that extends from an attachment point of the blade to a rotation mechanism to an outermost point of the blade, and the rotation mechanism having a second reference line that extends from an axis point of the rotation mechanism to the attachment point, wherein the blade rotates around the axis point, and wherein an angle between the first reference line and the second reference line is an acute angle. The apparatus further comprises a holding mechanism that causes the tissue sample to remain stationary while the blade makes, at least, a first rotation around the axis point, resulting in a first tissue section cut from the tissue sample.

A second aspect is directed to a method for cutting a tissue sample into a plurality of sections. The method comprises providing a blade having a first reference line that extends from an attachment point of the blade to a rotation mechanism to an outermost point of the blade, and the rotation mechanism having a second reference line that extends from an axis point of the rotation mechanism to the attachment point. The blade rotates around the axis point, and an angle between the first reference line and the second reference line is an acute angle. The method further comprises providing the tissue sample that remains stationary for at least a portion of a cutting process by way of a holding mechanism. The cutting process cuts the tissue sample into the plurality of sections. Additionally, the method includes, by way of the rotation mechanism, causing the blade to rotate such that a first rotation of the blade causes a first cut of the tissue sample that produces a first tissue section. The tissue sample, by way of the holding mechanism, remains stationary while the blade makes, at least, the first rotation.

A third aspect is directed to an apparatus for cutting a tissue sample into a plurality of sections. The apparatus comprises a blade having a first reference line that extends from an attachment point of the blade to a rotation mechanism to an outermost point of the blade, and the rotation mechanism having a second reference line that extends from an axis point of the rotation mechanism to the attachment point. The blade rotates around the axis point, and an angle between the first reference line and the second reference line is an acute angle. Furthermore, the tissue sample remains stationary while the blade makes, at least, a first rotation around the axis point producing a first tissue section. The blade rotates on a horizontal plane. The apparatus further comprises a motor that is coupled to the rotation mechanism that causes the blade to move from a first position associated with the first rotation to a second position associated with a second rotation.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer-readable media, for instance, database cluster 104. Computer-readable media can be any available media that may be accessed by server 102 and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote health care device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
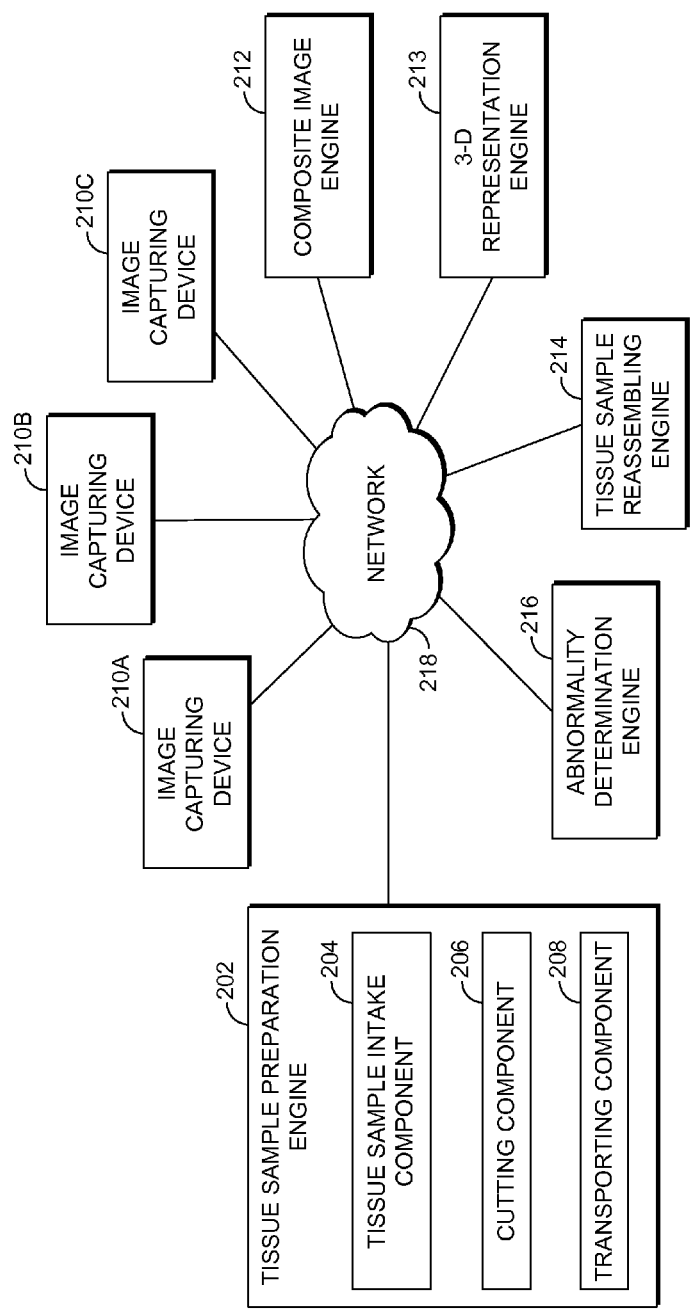
FIG. 2 depicts an exemplary system architecture suitable for implementing embodiments of the present invention.

Turning now to FIG. 2, an exemplary system architecture 200 suitable for implementing embodiments of the present invention is illustrated. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

The system 200 includes, among other components not shown, a tissue sample preparation engine 202, image capturing devices (210A, 210B, and 210C), a composite image engine 212, a three-dimensional (3-D) representation engine 213, a tissue sample reassembling engine 214, and an abnormality determination engine 216. Not all components shown in system 200 may be utilized in a particular system. Similarly, components not shown in system 200 may be utilized. System 200 is provided for exemplary purposes only, and is just one embodiment of the present invention. Generally, the components communicate by way of a network 218, which may be the network 106 described above with respect to FIG. 1.

The tissue preparation engine 202 is generally responsible for receiving a tissue sample and preparing the tissue sample for further processing. The tissue preparation engine 202 comprises a tissue sample intake component 204, a cutting component 206, and a transporting component 208. Tissue is a cellular organizational level intermediate between cells and a complete organ. A tissue is an ensemble of similar cells from the same origin that together carry out a specific function. As used herein, a tissue sample is any type of sample from a living or non-living entity. In embodiments, the tissue sample may include a collection of cells, fat, muscle, skin, etc. For example, for tissue sample from animals, the tissue sample may be one or more of connective, muscle, nervous, or epithelial tissue. For tissue sample from plants, the tissue sample may be one or more of epidermis, the ground tissue, or the vascular tissue. While referred to as a tissue sample, the actual tissue sample may first be embedded in wax, such as paraffin, prior to being processed using embodiments described herein. Further, in some embodiments, the paraffin-embedded tissue sample may have been embedded using a cassette, and therefore, the tissue sample received by the tissue sample intake component 204 may be embedded in wax, such as paraffin, and may also be attached to a cassette.

The tissue sample intake component 204 receives a tissue sample, retains the tissue sample in place, and aligns the tissue sample with a cutting mechanism. These may be done manually, or in embodiments, these tasks may be automated such that user intervention is not needed. In one embodiment, once the tissue sample is placed in an apparatus suited for receiving the tissue sample, user intervention may not be necessary until at least the tissue sample has been reassembled and is moved to a location for storage. Depending on the embodiment utilized, the tissue sample intake component 204 may also be responsible for moving the tissue sample in a particular direction to facilitate the cutting of the tissue sample into a plurality of sections. For instance, in one embodiment, once the cutting mechanism makes a first cut of the tissue sample to produce a first section, the tissue sample may be moved prior to the second cut of the tissue sample to produce a second sample. Alternatively, the tissue sample may be stationary throughout the entire process, and the cutting mechanism may not only rotate to make a cut through the tissue sample but may also move in a different direction in between cuts, such as between a first cut and a second cut of the tissue sample. The aligning of the tissue sample may be performed through the use of lasers, such as one or more, two or more, etc., lasers to align the tissue sample prior to the cutting process. In one embodiment, these lasers or other lasers may be used to identify the tissue sample being processed. For instance, the tissue sample (e.g., the cassette) may be labeled with an RFID tag, barcode, P-chip, or the like, which would allow the system to identify the tissue sample being processed.

The cutting component 206 is generally responsible for making cuts through the tissue sample to produce a plurality of tissue sections or slices. Again, this cutting process could be manual, but in embodiments, it is fully automated and does not require user intervention. A cutting mechanism that is controlled by the cutting component 206 generally comprises a blade and a rotation mechanism. The blade has a first reference line that extends from an attachment point of the blade to a rotation mechanism to an outermost point of the blade. The rotation mechanism has a second reference line that extends from an axis point of the rotation mechanism to the attachment point, where the blade rotates around the axis point. Further, the angle formed between the first and second reference lines may be an acute angle. More particularly, the angle formed may be from 10° to 80°, or from 20° to 60°, or from 30° to 40°. This angle enables just a portion of the blade to touch the tissue sample at first, and as the blade rotates around the axis, more of the blade eventually cuts through the tissue sample. In one embodiment, the blade is parallel to a horizontal surface and thus cuts horizontally through the tissue sample. However, other embodiments are also contemplated wherein the blade cuts vertically through the tissue sample, or even at an angle. The cutting mechanism will be discussed in more detail in regards to FIGS. 6 and 7. The cutting component 206 may make a determination or may be preset with data regarding how fast the blade is to rotate, how thick the sections are cut, etc. For instance, depending on the type of tissue sample being processed, the cutting component 206 may comprise logic that assists in a determination as to how thick the sections are to be cut, such as 3 µm, 5 µm, 10 µm, 20 µm, 50 µm, 100 µm, etc.

The transporting component 208 is generally responsible for facilitating the transportation of the cut sections of the tissue sample through the process. Once a first section is cut from the tissue sample block (e.g., the tissue sample embedded in wax), the first section is placed onto a transporting mechanism and is moved from a first location on the transporting mechanism to a second location. In one embodiment, the process of placing the tissue samples on the transporting mechanism is automated and is done without user intervention. In one embodiment, the transporting mechanism comprises a conveyor system. In a further embodiment, one or both of the blade or the transporting mechanism comprises a vacuum mechanism that provides suction to keep the tissue sections stationary as the tissue sections are moved from the blade to the transporting mechanism, and/or as they are moved on the transporting mechanism from a first location to a second location. The transporting component 208 may determine how fast the tissue sections are to move along the transporting mechanism (e.g., conveyor system), etc.

Image capturing devices 210A, 210B, and 210C are illustrated in the system 200. While three image capturing devices are illustrated, any number of these devices may be utilized, such as one or more image capturing devices. In some embodiments, multiple image capturing devices may be utilized to capture electronic images at different positions, angles, wavelengths, bands of spectrum, or the like. Image capturing devices 210A, 210B, and 210C may be any type of device that is capable of providing electronic images at the specifications required to provide an image that can be used by a medical professional to assist in determining if there are any abnormalities in the tissue or cells. For example, the image capturing devices may be charge-coupled devices that are configured to capture electromagnetic energy within different spectral bands. In one embodiment, the process of cutting the tissue sample block, transporting the cut sections, and taking images of the cut sections does not involve staining or generation of glass slides, as is typically the procedure with digital pathology systems.

As mentioned, in one embodiment, each of the image capturing devices 210A, 210B, and 210C utilized capture electromagnetic energy at different spectral bands, such as between 380-450 nm (violet) 450-495 nm (blue), 495-570 nm (green), 570-590 nm (yellow), 590-620 nm (orange), 620-750 nm (red), 750-900 nm (near infrared), 1550-1750 nm (mid-infrared), 2080-2350 nm (mid-infrared), 10400-12500 nm (thermal infrared), and the like. As such, not only may the image capturing devices 210A, 210B, and 210C capture electromagnetic energy within the visible spectrum (approximately 380-750 nm), but they may also operate outside of the visible spectrum, including ultraviolet, x-ray, infrared, microwave, radio, and the like. For example, if a particular system, such as system 200, has three image capturing devices 210A, 210B, and 210C, image capturing device 210A may capture electromagnetic energy within a spectral band of 450-495 nm, image capturing device 210B may capture electromagnetic energy within a spectral band of 620-750 nm, and image capturing device 210C may capture electromagnetic energy within a spectral band of 750-900 nm.

The images taken by the image capturing devices 210A, 210B, and 210C may be communicated to a composite image engine 212, which is generally responsible for taking the various images captured by the image capturing devices 210A, 210B, and 210C and generating one or more composite images for each section cut from the tissue sample block. As mentioned, multiple images may be taken of each of the tissue sections cut from the tissue sample block. These multiple images may be used to generate one or more composite images for each section. In one embodiment, each of the composite images is a single image. For example, image detail from a first image not found in other images taken of the same tissue section may be extracted and put into the composite image for that particular tissue section. This allows the composite image to have as much differing image detail as possible based on the images taken by the image capturing devices 210A, 210B, and 210C.

Once the composite images are generated, these composite images may be communicated to a 3-D representation engine 213, which associates each of the composite images to one another in a particular order corresponding to the order of the tissue sections cut from the tissue sample block. As such, the composite images generated by the composite image engine 212 are associated in such a way as to generate a 3-D representation of the tissue sample block. This allows a medical practitioner to view the 3-D representation of the tissue sample block and to make virtual cuts through the 3-D representation to view the composite images of the tissue sections at different angles, from different positions, etc. In one embodiment, a medical practitioner is able to virtually step through the tissue sample block (e.g., move from one tissue section to another) by way of the 3-D representation and view the tissue sections in order. In one embodiment, the individual images prior to being used for the composite image are also available to the medical practitioner for viewing. For example, if an image of a particular tissue section was taken by an image capturing device that is configured to capture electromagnetic energy within a spectral band of 495-570 nm, which would produce green visible light, this color may be of particular interest to the medical practitioner, and although this green image detail may be available by viewing the composite image, it may be more beneficial to view the green image detail by itself without other color detail.

In one embodiment, a medical practitioner may not require the use of the actual physical tissue sections, as the 3-D representation allows the medical practitioner to view each tissue section at different angles, with different spectrums of light, etc. The medical practitioner may utilize at least the colors of the 3-D representation to determine which tissue sections have potential abnormalities. In this embodiment, the physical tissue sections may not be stained or placed on slides, as is typically done, but instead the physical tissue sections may be reassembled for storage, as discussed below. However, in an alternative embodiment, a medical practitioner may utilize both the physical tissue sections (e.g., placed on glass slides) and the 3-D representation to make an accurate diagnosis of the patient based on the tissue sample.

The tissue sample reassembling engine 214 is generally responsible for reassembling the physical tissue sections after the sections have been processed by the other components described herein. In one embodiment, the tissue sections are not placed on glass slides, are not stained, etc., but it may be desired to save the tissue sections in case further analysis is needed in the future. As such, in these embodiments, the tissue sample reassembling engine 214 directs a reassembly mechanism to place each tissue section from the transporting mechanism to a reassembling surface, such as in a reassembly tray, and to place the tissue sections on top of one another in order to reform the tissue sample block prior to the block being cut. In this way, the reformed tissue sample block may be stored for further use. Storing the tissue sample block in this way takes up much less space than storing each tissue section separately, such as on a glass slide, as is typically done. If a medical practitioner should need to view any of the tissue sections at a later time, the reassembled tissue sample block may be re-cut or re-divided at that time.

The abnormality determination engine 216 is responsible for analyzing each of the images taken by the image capturing devices 210A, 210B, and 210C, or at least analyzing the composite image of each tissue section, and determining which tissue sections have potential abnormalities. If any potential abnormalities are detected, the abnormality determination engine 216 may provide an indication (e.g., flag the image) to the medical practitioner that the slide contains potential abnormalities. This provides decision support to the medical practitioner. In one embodiment, the abnormality determination engine 216 may indicate what the abnormality may be, which may assist the medical practitioner in determining what the abnormality is, a treatment plan, etc.

In one embodiment, the abnormality determination engine 216 takes the images and compares those images to known positives. The abnormality determination engine 216 may be programmed with images of known positives in different light, different wavelengths, etc. and with this comparison, the abnormality determination engine 216 is able to identify suspect areas from each image captured in the database. The abnormality determination engine 216 is also able to check for suspected areas in the combined images. Cells react to light in different ways, and as such, the suspected abnormal cells or areas would be identified by the way the light reacts to the cells. The database would have this information to compare the images, colors, wavelengths, or the like, of the cells reacting to the light and their appearance on the captured images. The system would have logic to identify these suspect areas, through comparison and matching.

Figure 3:
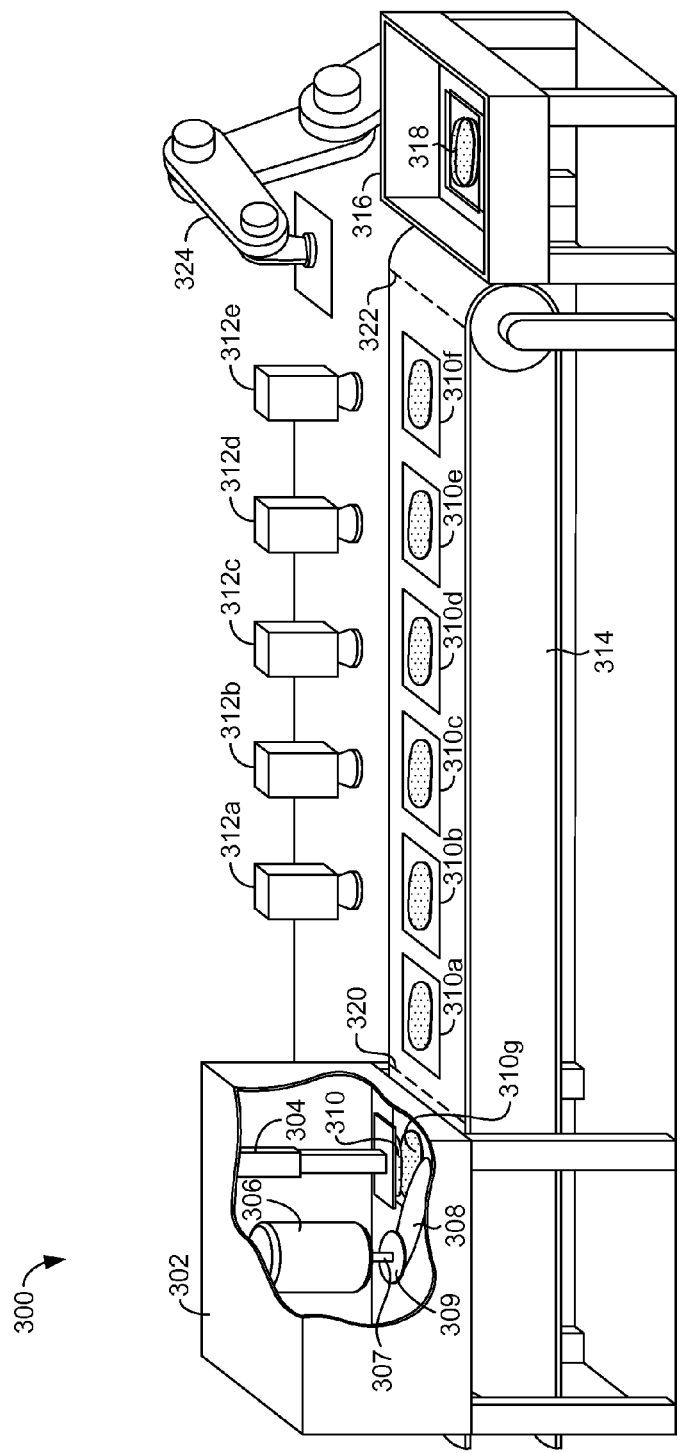
FIG. 3 depicts a perspective view of an automated tissue sample processing system, in accordance with an embodiment of the present invention.

FIG. 3 depicts a perspective view of an automated tissue sample processing system, in accordance with an embodiment of the present invention. Various components are illustrated in the system of FIG. 3, which is generally referred to herein as system 300. Other components not illustrated in system 300 may also be included, although not shown here. Additionally, some components illustrated in system 300 may not be used in embodiments provided herein. The components illustrated in system 300 include a housing 302, which houses a tissue sample intake mechanism 304 and a cutting mechanism, which comprises at least a motor 306, a shaft 307, a blade 308, and a rotation mechanism 309. The tissue sample intake mechanism 304 may receive a tissue sample 310 (e.g., a tissue sample embedded in wax and placed on a cassette) and may align the tissue sample 310 with the cutting mechanism, as shown in FIG. 3. In one embodiment, two or more lasers are used to align the tissue sample 310 with the cutting mechanism, ensuring that the blade 308 of the cutting mechanism makes contact with the tissue sample 310 in the correct location. Many different configurations of the tissue sample intake mechanism 304 are possible. For instance, in one embodiment, once the tissue sample 310 is placed on an intake surface, the process of aligning the tissue sample 310 with the cutting mechanism and holding the tissue sample 310 in place as the cutting mechanism makes multiple cuts through the tissue sample 310 may be completely automated, as not to require user intervention. In an alternative embodiment, the alignment of the tissue sample 310 with the cutting mechanism may require user intervention.

In embodiments, once the tissue sample 310 has been aligned with the cutting mechanism, the process of holding the tissue sample 310 in place during the cutting of the tissue sample 310 is automated. As briefly mentioned herein, in one aspect, the tissue sample remains stationary throughout the entire cutting process, including in between cuts. In this embodiment, the cutting mechanism moves from one position to another position in between cuts, allowing for subsequent cuts to be made at different locations of the tissue sample 310. For example, if the tissue sections are to be 10 µm thick, the blade 308 of the cutting mechanism would be moved by 10 µm in one direction after a first cut or a first rotation of the blade 308, then would be moved by another 10 µm in that same direction after a second cut or a second rotation of the blade 308, and so on. However, in an alternative embodiment, the tissue sample intake mechanism 304 still holds the tissue sample 310 in place while the cutting mechanism makes each cut, but between cuts or rotations of the blade 308, the tissue sample 310 is moved in a particular direction and by a certain distance, allowing the cutting mechanism to cut the tissue sample 310 at different positions, which produces the plurality of tissue sections. For example, if the tissue sections are to be 10 µm in thickness, after a first cut or a first rotation of the blade 308, the tissue sample intake mechanism 304 or some other component of the system would cause the tissue sample to be moved in a certain direction by 10 µm, and after a second cut or a second rotation of the blade 308, the tissue sample 310 would be caused to move in that same direction by another 10 µm, and so on. In this embodiment, a motor (not shown) may be utilized to move the tissue sample in between cuts.

The tissue sample intake mechanism 304 may comprise a holding plate 305. In the embodiment of FIG. 3, the holding plate 305 holds the tissue sample firmly so that the tissue sample does not move during the entire cutting process. An alternative embodiment where the tissue sample is moved in between cuts is described further in relation to FIG. 8.

As shown in FIG. 3, the cutting mechanism has made multiple cuts through the tissue sample to produce tissue sections 310a, 310b, 310c, 310d, 310e, 310f, 310g, and the other tissue sections that have been reassembled in the reassembly tray 316 to form at least a portion of a reformed tissue sample 318. As shown, once the cutting mechanism has made a cut through the tissue sample 310, the tissue section, which here is tissue section 310g, is dropped or placed onto the transporting mechanism 314. The transporting mechanism 314, as shown in FIG. 3, may take the form of a conveyor system that transports each of the tissue sections from at least a first location to at least a second location along the surface of the conveyor system. As defined herein, the first location may be any location along reference line 320, such as prior to the capturing of the images of the tissue sections. The second location may be any location along reference line 322, such as subsequent to the capturing of the images of the tissue sections.

In laboratory scenarios where tissue sections are very small in thickness, it becomes increasingly important to take extra care in moving a tissue section from one location to another location, as the tissue sections may be chaffed or destroyed easily. As such, in various embodiments, one or more of the blade 308, a portion of the tissue sample intake mechanism 304, or the transporting mechanism 314 has a vacuum component to cause the tissue section to remain in place. For example, in one embodiment, the blade 308 may make a cut through the tissue sample 310 and also transport the tissue section to the transporting mechanism 314. In another embodiment, the tissue sample intake mechanism 304 has a vacuum component on the holding surface 305 that makes contact with the tissue sections after each cut. For instance, a bottom surface of the holding surface 305 may utilize a vacuum to hold the tissue sections in place as the tissue sections are being moved to the transporting mechanism 314. In yet another embodiment, the blade 308 cuts the tissue sample 310 on a bottom portion of the tissue sample such that when a cut is made, the tissue sample 310 drops a very short distance onto a surface 313 of the transporting mechanism 314. The system is configured so that the tissue section would drop such a short distance that the tissue section would not be destroyed as it moves onto the surface 313 of the transporting mechanism 314.

In yet another embodiment, a surface 313 of the transporting mechanism 314 uses a vacuum to hold the tissue sections (310a-310g) in place as the tissue sections move from a first location to a second location on the transporting mechanism 314. In an embodiment, any combination of the above-mentioned embodiments is used to provide a safe transfer of the tissue sections onto the transporting mechanism.

Reassembly mechanism 324 is generally responsible for moving each of the tissue sections from the transporting mechanism 314 onto the reassembly tray 316. As discussed above, various components of the system 300 may have vacuum components that facilitate the transfer of the tissue sections from one location to another. Here, in one embodiment, the reassembly mechanism 324 comprises a vacuum component on a bottom surface of a transport plate 325 to ensure that the tissue sections are not destroyed during the transfer from the transporting mechanism 314 to the reassembly tray 316. In the embodiment of system 300, the vacuum component may be present on the bottom surface of the transport plate 325 that makes contact with the tissue sections. In this embodiment, the transport plate 325 is sized such that it is at least the size of the tissue sections. It should be noted that the reassembly mechanism 324 of FIG. 3 is just one of many possible configurations that could be used to transport the tissue sections from the transporting mechanism 314 to the reassembly tray 316.

The system 300 also comprises image capturing devices 312a, 312b, 312c, 312d, and 312e. While five image capturing devices are illustrated in FIG. 3, any number of devices could be used. The determination of the quantity of image capturing devices used may be dependent upon, at least, the type of image capturing devices used, such as whether the image capturing devices are capable of capturing electromagnetic energy within various spectral bands. In one embodiment, a single image capturing device is utilized, such as a device that is configured to capture electromagnetic energy within a large spectral band. In another embodiment, two or more image capturing devices are utilized. In embodiments, each of the image capturing devices 312a, 312b, 312c, 312d, and 312e capture electromagnetic energy within a different spectral band, such as between 380-450 nm (violet), 450-495 nm (blue), 495-570 nm (green), 570-590 nm (yellow), 590-620 nm (orange), 620-750 nm (red), 750-900 nm (near infrared), 1550-1750 nm (mid-infrared), 2080-2350 nm (mid-infrared), 10400-12500 nm (thermal infrared), and the like. One or more of the image capturing devices 312a, 312b, 312c, 312d, and 312e may have the capability of capturing images at different angles, so that when the 3-D representation is compiled, the medical practitioner is able to view the tissue sample as a whole and the tissue sections at many different angles, assisting in the identification of potential abnormalities. In embodiments, the image capturing devices 312a, 312b, 312c, 312d, and 312e are high-speed devices. Further, the image capturing devices 312a, 312b, 312c, 312d, and 312e may include sensors so that the image capturing devices 312a, 312b, 312c, 312d, and 312e take the images at the correct times. Additionally, the image capturing devices 312a, 312b, 312c, 312d, and 312e may take images at varying magnitudes, such as 10×, 90×, 120×, etc.

While not pictured in FIG. 3, a light emitting source may be utilized to emit electromagnetic radiation (e.g., photons) at different wavelengths. For example, a light emitting source may emit electromagnetic radiation within a spectral band of about 400-750 nm, which produces visible light. Another light emitting source may emit electromagnetic radiation within a spectral band of 750-900 nm, which is near infrared. In one embodiment, a single light emitting source is used, but in alternative embodiments, two or more light emitting sources are used. The light emitting source enable back lighting of the tissue sections, or may be located on or near the image capturing devices. The light emitting sources may be located in a number of different locations, and thus all such possibilities that would enable electromagnetic radiation to hit the surface of the tissue sections are contemplated to be within the scope of the present invention. The light emitting source may be a natural light source, or a synthetic light source.

Figure 4:
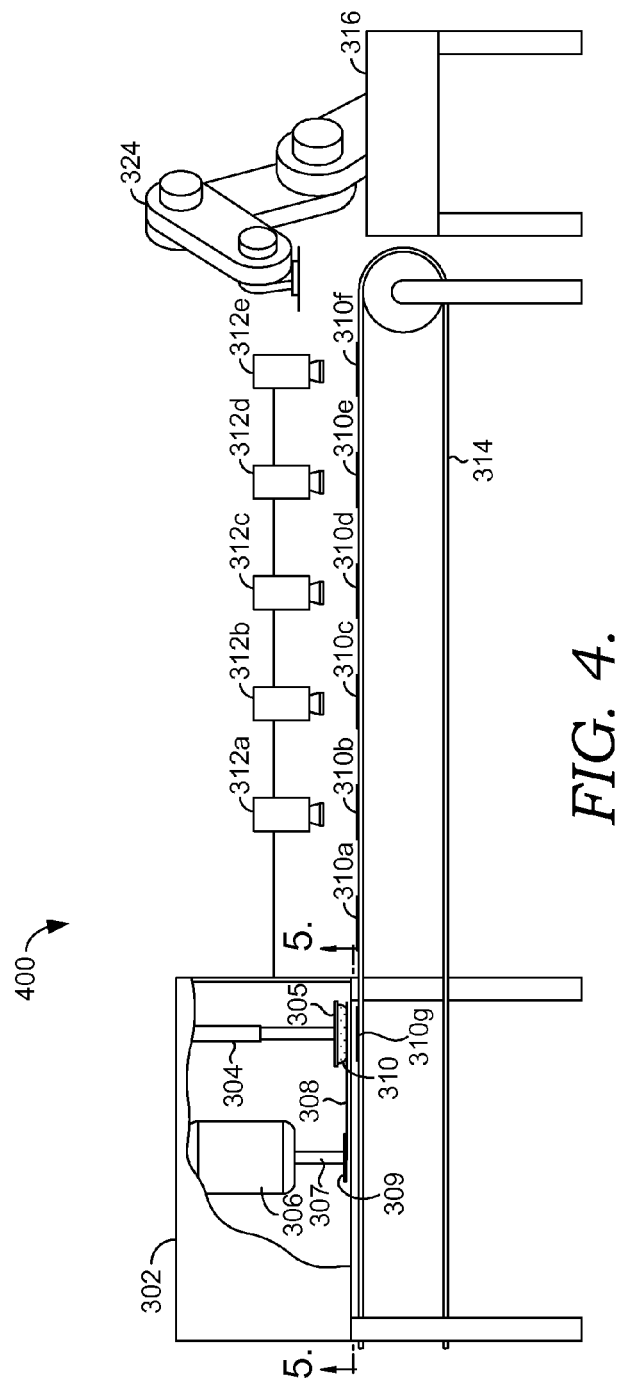
FIG. 4 depicts a side elevational view of an automated tissue sample processing system, in accordance with an embodiment of the present invention.

FIG. 4 depicts a side elevational view of an automated tissue sample processing system 400, in accordance with an embodiment of the present invention. The components shown in FIG. 4 are the same as those of FIG. 3 but shown from a side elevational view. As mentioned with respect to FIG. 3, components not shown in FIG. 4 are contemplated to be within the scope of the present invention, when needed to carry out embodiments described herein. Further, some components illustrated in FIG. 4 may not be used in some embodiments described herein. The configuration of each of the components shown in FIG. 4 is for exemplary purposes only. For instance, the reassembly mechanism 324 and the tissue sample intake mechanism 304 may be configured differently in some embodiments. All of these alternative configurations are contemplated to be within the scope of aspects of the present invention.

Figure 5:
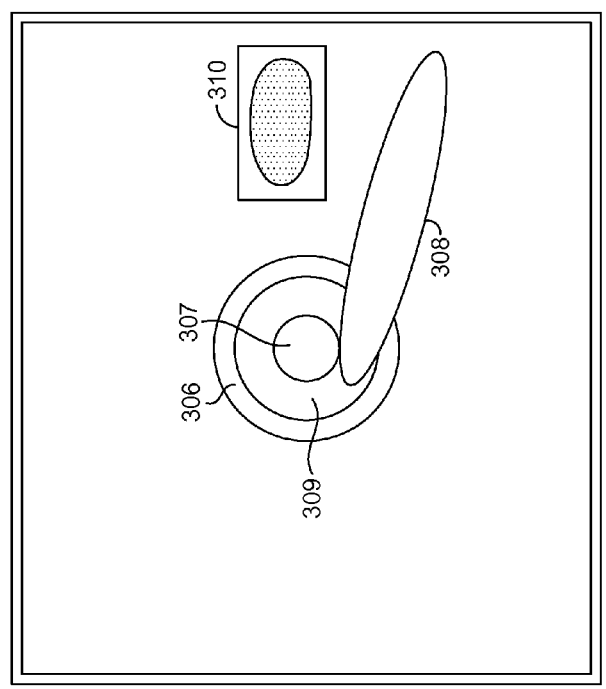
FIG. 5 depicts a bottom plan view of a tissue sample processing unit, in accordance with an embodiment of the present invention.

FIG. 5 depicts a bottom plan view of a tissue sample processing unit, in accordance with an embodiment of the present invention. As shown, the tissue sample processing unit of FIG. 5 is generally referred to herein as system 500, and comprises a shaft 307, a rotation mechanism 309, a motor 306, a blade 308, and the tissue sample block 310. As shown, the blade 308 rotates around an axis point of the rotation mechanism 309, which will be explained in more detail herein in relation to FIGS. 6 and 7.

Figure 6:
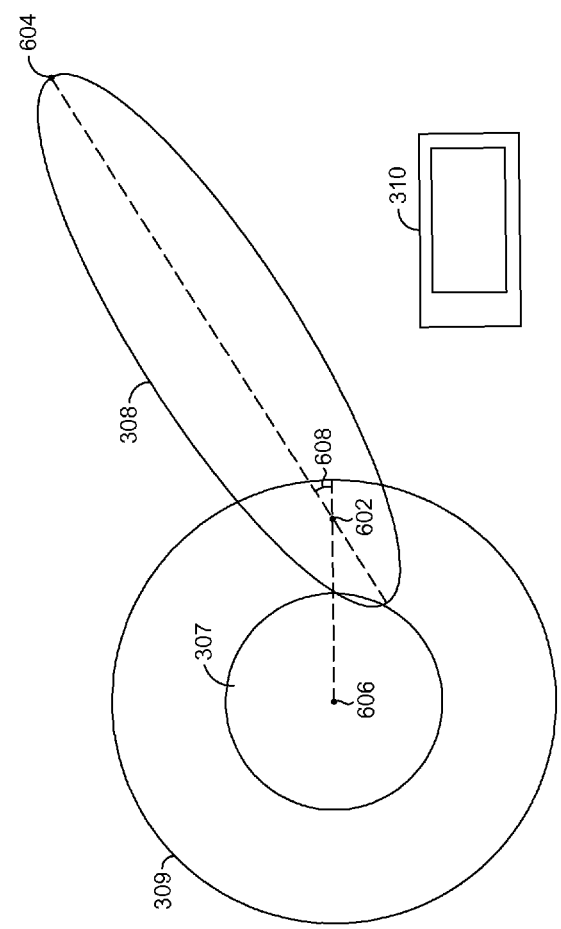
FIG. 6 depicts a bottom plan view of a cutting mechanism used to cut a tissue sample into a plurality of sections, in accordance with an embodiment of the present invention.

FIG. 6 depicts a bottom plan view of a cutting mechanism used to cut a tissue sample into a plurality of sections, in accordance with an embodiment of the present invention. The cutting mechanism comprises rotation mechanism 309, shaft 307, and blade 308. It is noted that the shape of the blade 308 may vary, and the shape shown in FIG. 6 is provided for illustrative purposes only. Further, the configuration of the cutting mechanism may also vary, and the components of the cutting mechanism shown in FIG. 6 are provided for illustrative purposes only. In this embodiment, the blade 308 rotates around the shaft 307 as it makes cuts into the tissue sample. For example, in one embodiment, each cut that produces a tissue section is associated with a rotation of the blade 308 around the shaft 307. The shaft 307, being coupled to the motor, enables movement of the blade 308 around the shaft 307. As shown in FIG. 6, the blade 308 is in a horizontal position and is angled such that only a small portion of the blade 308 initially makes contact with the tissue sample 310. While typically the blade is stationary and the tissue sample is moved to make contact with the blade, herein, the blade rotates, and in some embodiments, the entirety of the blade does not initially make contact with the tissue sample. Instead, a first contact of the blade 308 and the tissue sample 310 comprises just a first portion of the blade 308 making contact with the tissue sample 310.

In one embodiment, the blade 308 has a first reference line that extends from an attachment point 602 of the blade to a rotation mechanism 309 to an outermost point 604 of the blade. The rotation mechanism 309 has a second reference line that extends from an axis point 606 of the rotation mechanism 309 to the attachment point 602. A shown in FIG. 6, an angle 608 formed between the first and second reference lines is, in one embodiment, an acute angle. More particularly, the angle 608 is from 10° to 80°, or from 20° to 60°, or from 30° to 40°. The actual angle used may be dependent upon the type of tissue sample being cut, the type of blade used, the size of the blade, the size of the rotation mechanism 309, the speed of the blade rotation, etc. In embodiments, this angle formed between the first and second reference lines persists even as the blade 308 rotates around the axis point 606 or around the shaft 307. While in one embodiment the angle discussed above is formed between the first and second reference lines, in another embodiment, the angle is measured between the first reference line and a surface of the tissue sample block, such as a reference line along the surface of the tissue sample block with which the blade 308 first makes contact. In one instance, this reference line is horizontal, or is parallel to a horizontal surface on which the tissue sample block sits.

Figure 7:
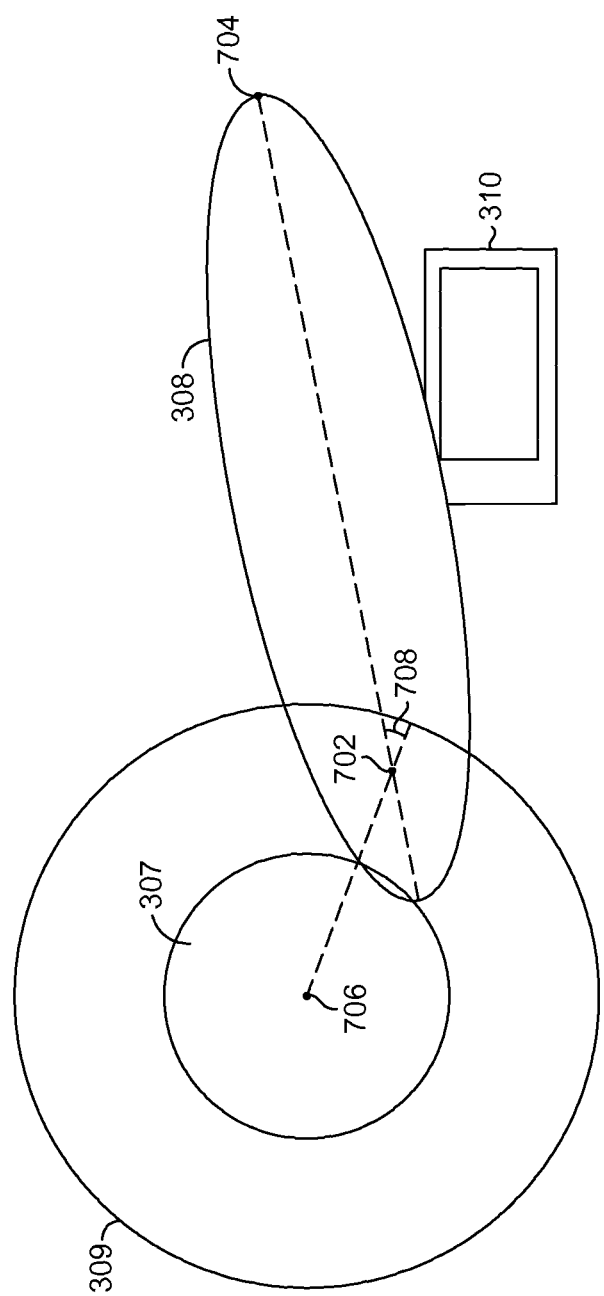
FIG. 7 depicts a bottom plan view of a cutting mechanism used to cut a tissue sample into a plurality of sections, in accordance with an embodiment of the present invention.

FIG. 7 depicts a bottom plan view of a cutting mechanism used to cut a tissue sample into a plurality of sections, in accordance with an embodiment of the present invention. The cutting mechanism of FIG. 7 is similar to that of FIG. 6, but here, the blade 308 is shown making a cut into the tissue sample 310. As discussed above with respect to FIG. 6, in one embodiment, the angle 708 formed between the first reference line and the second reference line persists as the blade 308 rotates around the shaft 307 or the axis point 706. As mentioned, the first reference line extends from an attachment point 702 of the blade 308 to the rotation mechanism 309 to an outermost point 704 of the blade 308, and the second reference line extends from an axis point 706 of the rotation mechanism 309 to the attachment point 702. While the axis point 706 is described as being a part of the rotation mechanism 309, as shown in FIG. 7, the axis point 706 is on a bottom surface of the shaft 307. However, when we speak of rotation mechanism 309, in some embodiments, this term extends to the shaft 307 and the motor as well, as all of these components contribute to the rotation of the blade 308 around the axis point 706. The blade 308 may comprise an edge that is sharp enough to cut through the tissue sample 310. Different portions of this edge, as previously described, may make contact with the tissue sample 310 at different times. For instance, because of the angle discussed herein between the first and second reference lines, the cutting edge of the blade 308 is able to make a smooth cut through the tissue sample without unnecessarily tearing or even destroying the tissue sections that are produced as a result of the cuts.

Figure 8B:
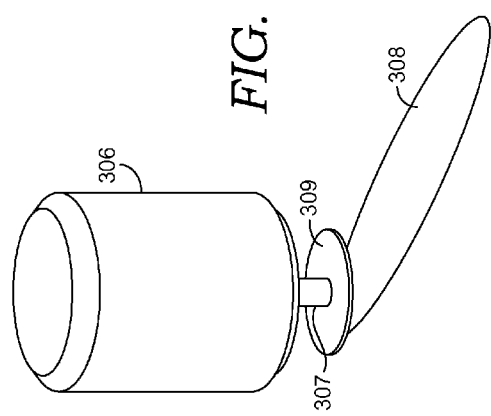
FIGS. 8A and 8B depict a cutting mechanism having a blade and a rotation mechanism that move in between cuts of a tissue sample, in accordance with an embodiment of the present invention.
Figure 8A:
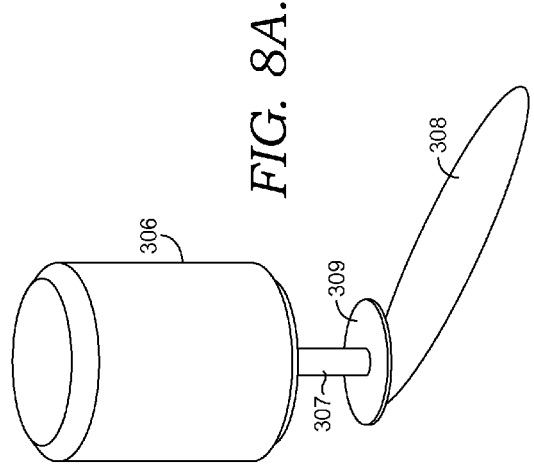

Turning now to FIGS. 8A and 8B, a cutting mechanism is shown having a blade and a rotation mechanism that move in between cuts of a tissue sample, in accordance with an embodiment of the present invention. FIG. 8A depicts the rotation mechanism 309 and the blade 308 in a first position associated with a first cut or a first rotation of the blade 308 around an axis point. In the embodiment of FIGS. 8A and 8B, the tissue sample remains stationary throughout the cutting process such that the blade 308 is moved from one cut of the tissue sample to another so that multiple tissue sections can be cut from the tissue sample. FIG. 8A illustrates the rotation mechanism 309 and the blade 308 in a first position, while FIG. 8B illustrates the rotation mechanism 309 and the blade 308 in a second position. In embodiments, the motor and the shaft 307 cause the rotation mechanism 309 and the blade 308 to move, in this case, vertically, but in other embodiments, a separate motor may be used for this purpose.

Figure 9:
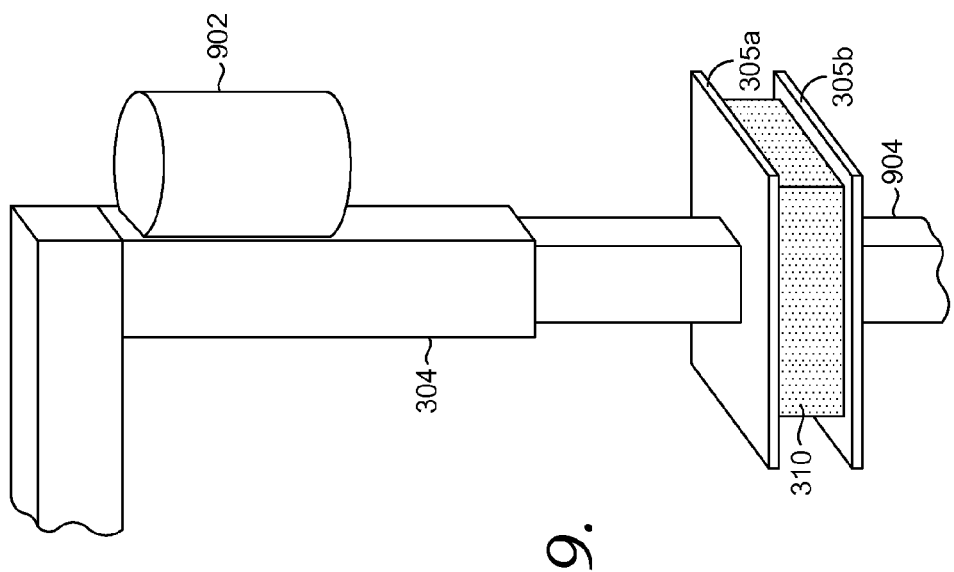
FIG. 9 depicts a tissue sample intake mechanism that causes a tissue sample to move in between cuts of the tissue sample, in accordance with an embodiment of the present invention.

FIG. 9 depicts a tissue sample intake mechanism 304 that causes a tissue sample to move in between cuts of the tissue sample, in accordance with an embodiment of the present invention. The tissue sample intake mechanism 304 comprises a top holding plate 305a and a bottom holding plate 305b. The tissue sample 310 may be moved, in this case, vertically, by way of a motor 902 coupled to a shaft 904. The top holding plate 305a and the bottom holding plate 305b hold the tissue sample 310 tightly, not allowing any or much movement during cuts. In one embodiment, instead of the tissue sections dropping down onto a surface of the transporting mechanism, as shown in FIGS. 3 and 4, a bottom surface of the top holding plate 305a comprises a vacuum that holds a tissue section against this bottom surface while the tissue section is being transported onto a surface of the transporting mechanism. Many other configurations are possible to move a tissue section that has been cut from a tissue sample onto a transporting mechanism, and are contemplated to be within the scope of the present invention. The configuration of FIG. 9 is intended to be exemplary in nature, and not limiting.

FIG. 10 is a flow diagram of a method 1000 for performing automated digital processing of a tissue sample, in accordance with an embodiment of the present invention. Initially, a tissue sample that is to be processed to produce a 3-D representation of the tissue sample is received, shown at block 1002. At block 1004, the tissue sample is aligned with a cutting mechanism, such as by two or more lasers. In one embodiment, at least three lasers are used to align the tissue sample with the cutting mechanism. The cutting mechanism may comprise a blade that is coupled to a rotation mechanism such that the blade makes at least a first rotation around an axis point of the rotation mechanism while the tissue sample remains stationary. In one embodiment, the tissue sample remains stationary throughout the entire cutting process, even between cuts. In an alternative embodiment, the tissue sample remains stationary during each cut, but is moved before each subsequent cut so that the blade cuts at a different location on the tissue sample for each cut. At block 1006, a plurality of sections of the tissue sample are caused to be produced, such as by the cutting mechanism making a plurality of cuts through the tissue sample at different locations. Each section is received at a transporting mechanism, shown at block 1008. Each of the tissue sections are moved from a first location along a first reference line to at least a second point along a second reference line on a surface of the transporting mechanism. In one embodiment, the transporting of the tissue sections is done without user intervention. The transporting mechanism may comprise a conveyor system that is automated to move the tissue sections along the conveyor. As such, the surface of the transporting mechanism may be a surface of the conveyor. In one instance, the conveyor may comprise a vacuum component to facilitate the tissue sections remaining stationary relative to the surface of the transporting mechanism At block 1010, electronic images of each tissue section are captured using image capturing devices, such as between the first location and the second location on the surface of the transporting mechanism. At least one of the image capturing devices may capture electromagnetic energy within a different spectral band than other image capturing devices used. While in one embodiment a single image capturing device is used that can capture electromagnetic energy within various spectral bands, in another embodiment, two or more image capturing devices are used. Even though the image capturing devices are capturing images of the tissue sections at different spectral bands, such as is the case in one embodiment, the tissue sections in embodiments remain unstained. Typically, tissue sections cut from a tissue sample block are stained and placed on glass slides prior to being analyzed. However, here, the tissue sections may not be stained at all throughout the entire process described herein.

At block 1012, the images captured by the image capturing devices are compiled for each tissue section to generate a composite image for each tissue section. At block 1014, a 3-D representation of the tissue sample is generated using the composite images of the tissue sections. In one embodiment, the 3-D representation of the tissue sample can be virtually cut so that a medical practitioner can look at the tissue sections from various angles, positions, color, etc., to identify potential abnormalities.

In one embodiment, once the tissue sections have been moved along the surface and the images have been captured, the tissue sections may be reassembled by a reassembling mechanism to produce a reformed tissue sample. For instance, the tissue sample may be embedded in wax (e.g., paraffin), and as such, when reformed, the tissue sample may be reformed into a block that looks like the tissue sample block prior to being cut. Advantages of reassembling the tissue sample block are to store more efficiently the tissue sections that have been cut and to be able to retrieve the reformed tissue sample block if needed in the future.

FIG. 11 is a flow diagram of another method 1100 for performing automated digital processing of a tissue sample, in accordance with an embodiment of the present invention. At block 1102, a tissue sample is provided that is to be processed by way of an automated digital processing system. As mentioned, when we refer to a tissue sample herein, the tissue sample may be embedded in a solid substance, such as wax (e.g., paraffin). At block 1104, the tissue sample is cut into a plurality of sections. In one embodiment, the tissue sample is caused to remain stationary while at least a first section of the plurality of sections is cut. The tissue sample may remain stationary during subsequent cuts in the case where the cutting mechanism is configured to move to cut the tissues sample at different locations. For example, in this embodiment, the cutting mechanism moves from a first position to a second position between a first cut corresponding to a first section of the tissue sample and a second cut corresponding to a second section of the tissue sample. Alternatively, the tissue sample may move in between cuts.

At block 1106, a transporting mechanism is utilized to move each tissue section along a surface of the transporting mechanism, such as from a first location to a second location on the transporting mechanism. The transporting mechanism may include a conveyor system, such as a conveyor system that utilizes a vacuum to hold the tissue sections to a surface of the transporting mechanism while the tissue sections are moved along the surface. Electronic images of each tissue section of the tissue sample are captured at block 1108. In one embodiment, these electronic images are captured by image capturing devices between the first and second locations. In embodiments, the tissue sections cut from the tissue sample are not stained during the process described herein. Instead of using staining to identify abnormalities, image capturing devices capturing light at different wavelengths are used to identify potential abnormalities. In embodiments, the electronic images for each tissue section are compiled to generate a composite image for each section. Once the composite images are generated, a 3-D representation of the tissue sample is generated based on the composite images.

At block 1110, the plurality of tissue sections of the tissue sample are reassembled to reform the tissue sample embedded in the wax. In embodiments, the storage of the tissue sample is much more efficient when stored as a reassembled block. At some time, a medical practitioner may even want to look at the physical tissue sample, such as at a particular tissue section, and can retrieve the reformed tissue sample from storage for viewing and analysis.

FIG. 12 is a flow diagram of another method 1200 for performing automated digital processing of a tissue sample, in accordance with an embodiment of the present invention. At block 1202, electronic images of each of a plurality of tissue sections of a tissue sample are captured by way of, for instance, one or more image capturing devices. The tissue sections are cut from the tissue sample by way of a cutting mechanism. In embodiments, the tissue sections remain unstained throughout the process. At block 1204, the electronic images are analyzed, such as by an abnormality determination engine, for potential abnormalities in the tissue sample that is being processed. Potential abnormalities in the tissue sample may comprise abnormal cells that could indicate that the patient has a particular disease or other condition. The potential abnormalities may be discovered by way of a macroscopic or microscopic examination of the plurality of sections utilizing the image capturing devices. One or more of the electronic images are identified as indicating potential abnormalities in the corresponding section of the tissue sample, shown at block 1206. At block 1208, an indication is provided that the one or more electronic images indicate potential abnormalities. In one embodiment, this indication is a flag for the medical practitioner viewing and analyzing the electronic images, indicating to the medical practitioner to take a closer look at those flagged images.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. An apparatus for cutting a tissue sample into a plurality of sections, the apparatus comprising:
   a cutting mechanism comprising:
   1) a blade having a first reference line that extends from an attachment point of the blade to a rotation mechanism to an outermost point of the blade, and
   2) the rotation mechanism having a second reference line that extends from an axis point of the rotation mechanism to the attachment point, wherein the blade rotates around the axis point, and wherein an angle between the first reference line and the second reference line is an acute angle;
   a holding mechanism that causes the tissue sample to remain stationary while the blade makes, at least, a first rotation around the axis point, resulting in a first tissue section cut from the tissue sample.

2. The apparatus of claim 1, further comprising a motor that is coupled to a shaft that causes the holding mechanism that holds the tissues sample to move from a first position associated with the first rotation to a second position associated with a second rotation.

3. The apparatus of claim 2, wherein the first rotation produces a first tissue section, and wherein the second rotation produces a second tissue section.

4. The apparatus of claim 1, further comprising a motor that is coupled to the rotation mechanism by way of a shaft, the motor and the shaft causing the blade to move along an axis that is substantially perpendicular to an axis around which the blade rotates between the first rotation and a second rotation.

5. The apparatus of claim 1, wherein the tissue sample remains stationary from the first rotation of the blade to a second rotation of the blade.

6. The apparatus of claim 1, wherein the acute angle is from 10° to 80°.

7. The apparatus of claim 1, wherein the acute angle is from 20° to 60°.

8. The apparatus of claim 1, wherein the acute angle is from 30° to 40°.

9. An apparatus for cutting a tissue sample into a plurality of sections, the apparatus comprising:
   a blade having a first reference line that extends from an attachment point of the blade to a rotation mechanism to an outermost point of the blade;
   the rotation mechanism having a second reference line that extends from an axis point of the rotation mechanism to the attachment point,
   wherein the blade rotates around the axis point,
   wherein an angle between the first reference line and the second reference line is an acute angle,
   wherein the tissue sample remains stationary while the blade makes, at least, a first rotation around the axis point producing a first tissue section, and
   wherein the blade rotates on a horizontal plane; and
   a motor that is coupled to the rotation mechanism that causes the blade to move from a first position associated with the first rotation to a second position associated with a second rotation.

10. The apparatus of claim 9, further comprising a holding mechanism that causes the tissue sample to remain stationary while the blade makes, at least, a first rotation around the axis point.

11. The apparatus of claim 9, wherein blade moves from the first position to the second position along a vertical plane.

12. The apparatus of claim 9, wherein the motor and the shaft cause the blade to move along an axis that is substantially perpendicular to an axis around which the blade rotates between the first rotation and the second rotation.

* * * * *